United States Patent
Kase

[19]

[11] Patent Number: 5,861,348
[45] Date of Patent: *Jan. 19, 1999

[54] BODY-ADHESIVE TAPE

[75] Inventor: Kenzo Kase, Tokyo, Japan

[73] Assignee: Kinesio Co., Ltd., Japan

[*] Notice: This patent issued on a continued prosecution application filed under 37 CFR 1.53(d), and is subject to the twenty year patent term provisions of 35 U.S.C. 154(a)(2).

[21] Appl. No.: 716,572

[22] Filed: Sep. 19, 1996

[30] Foreign Application Priority Data

Jul. 23, 1996 [JP] Japan ................................. 8-210469

[51] Int. Cl.$^6$ ............................. B32B 7/12; A61F 13/00
[52] U.S. Cl. ........................ 442/184; 442/199; 442/254; 442/218; 428/195; 428/343; 428/355 AC; 602/55; 602/54; 602/903; 604/389
[58] Field of Search ............................. 602/55, 54, 903; 604/389, 307, 308; 442/184, 189, 199, 200, 203, 218, 254; 428/195, 343, 355, 355 AC

[56] References Cited

U.S. PATENT DOCUMENTS

| | | | |
|---|---|---|---|
| 2,310,082 | 2/1943 | Holbrooke | 602/55 |
| 2,349,709 | 5/1944 | Evans | 602/55 X |
| 2,399,545 | 4/1946 | Davis | 604/389 |
| 2,940,868 | 6/1960 | Patchell | 602/55 X |
| 3,199,548 | 8/1965 | Conant | 442/184 X |
| 3,457,919 | 7/1969 | Harbarcl | 602/55 |
| 3,618,754 | 11/1971 | Hoey | 206/59 C |
| 4,428,808 | 1/1984 | Schäfer et al. | 442/184 X |
| 5,230,701 | 7/1993 | Meyer et al. | 602/76 |
| 5,397,298 | 3/1995 | Mazza et al. | 602/903 X |

FOREIGN PATENT DOCUMENTS 5-45335  11/1993  Japan .

*Primary Examiner*—Daniel Zirker
*Attorney, Agent, or Firm*—Morrison Law Firm

[57] ABSTRACT

The present invention provides a body-adhesive tape having adhesive properties preventing the tape from peeling off due to sweat when it is applied in an overlapped manner, and which also has good moisture permeability. In the body-adhesive tape, a base cloth is formed from a stretchable warp thread and a standard weft thread. On one side of the base cloth a plurality of pressure-sensitive adhesive layers are formed separated by appropriate gaps. The pressure-sensitive adhesive layers are formed so that they meander left and right along the length of the tape. At the gaps, the base cloth is exposed so there is permeability. Since the gap meanders, it is longer than the tape, and thus there is more exposure of the weave and more permeability. The pressure-sensitive adhesive layers meander so that the tape can be attached anywhere on the body and can respond to tension due to body movement from any direction. Base cloth is processed for water repellency so that the tapes can be attached in an overlapping manner and no sweat or the like will be absorbed, and the upper tape will not tend to peel off.

2 Claims, 4 Drawing Sheets

BODY-ADHESIVE TAPE

BACKGROUND

The present invention relates to a body-adhesive tape. In particular, the present invention relates to a body-adhesive tape directly adhered to the skin in order to serve as a supporter for preventing injury to the muscles and the like in sports.

Conventionally, it has been well known that injuries can result during sports due to excessive force from muscles and the like. For this reason, various types of supporters are used. However, since supporters have fixed shapes, regions that were not covered by the supporters were not adequately protected. Tape-shaped supporters started to be used because of this. For example, in Japanese utility model examined publication number 5-45335, the present inventor disclosed an adhesive stretch supporter.

Two problems were discovered in the use of the adhesive stretch supporter described above. One was that when the supporters were adhered by crossing and overlapping them in an X shape or the like, sweat could soak in and cause the upper tape of the overlapping tapes to peel off. The other problem was that the mechanical method for opening holes did not achieve acceptable results in terms of providing permeability. Increasing the strength of the adhesive was considered as a way to prevent the upper tape from peeling off. However, increasing the strength of the adhesive can have an effect on the skin. These problems were considered and the present invention was developed with the object of providing a body-adhesive tape that can be adhered in an overlapping manner and that has superior permeability.

OBJECTS AND SUMMARY OF THE INVENTION

The object of the present invention is to overcome the problems of the prior art described above and to provide a body-adhesive tape that can be adhered in an overlapping manner and that has superior permeability.

Another object of the present invention is to provide a body-adhesive tape including; a base cloth formed from a warp thread and a weft thread, the warp thread including a stretch thread twisted together with a standard fiber, the weft thread being a normal thread, a plurality of strip-shaped pressure-sensitive adhesive layers formed on one side of the base cloth, the adhesive layers arranged in rows separated by prescribed gaps, the adhesive layers being strips meandering left and right along a length of the tape, the base cloth having low permeability at portions on which the pressure-sensitive adhesive layers are formed, and the base cloth having high permeability at the prescribed gaps separating the adhesive layers.

Another object of the present invention is to provide a body-adhesive tape, including; a base cloth having a width and a length, the base cloth having an elasticity along the length, and an adhesive layer disposed discontinuously on the base cloth to form an adhesive layer pattern alternating adhesive covered cloth with exposed cloth.

Another object of the present invention is to provide a body-adhesive tape, including; a base cloth having a width and a length, the base cloth having an elasticity along the length, an adhesive layer disposed discontinuously on the base cloth to form an adhesive layer pattern alternating adhesive covered cloth with exposed cloth, and the adhesive layer pattern is wave shaped parallel strips of adhesive covered cloth alternating with parallel shaped strips of exposed cloth.

Another object of the present invention is to provide a body-adhesive tape, including; a base cloth having a width and a length, the base cloth having an elasticity along the length, an adhesive layer disposed discontinuously on the base cloth to form an adhesive layer pattern alternating adhesive covered cloth with exposed cloth, the base cloth is an elasticized warp thread coarsely woven with a standard weft thread, and the elasticized warp thread is at least one selected from the group consisting of an elastic rubber thread spun with a standard fiber thread, a kinked fiber thread, stretchable synthetic monofilament, and a stretchable synthetic multifilament thread.

Another object of the present invention is to provide a body-adhesive tape, including; a base cloth having a width and a length, said base cloth having an elasticity along said length, an adhesive layer disposed discontinuously on said base cloth to form an adhesive layer pattern alternating adhesive covered cloth with exposed cloth, the adhesive layer pattern is wave shaped parallel strips of adhesive covered cloth alternating with parallel shaped strips of exposed cloth, the base cloth is an elasticized warp thread coarsely woven with a standard weft thread, and the elasticized warp thread is at least one selected from the group consisting of an elastic rubber thread spun with a standard fiber thread, a kinked fiber thread, stretchable synthetic monofilament, and a stretchable synthetic multifilament thread.

The present invention includes a body-adhesive tape wherein; a fabric comprising a warp formed by twisting a stretch thread and a normal thread and a weft formed from a normal thread serves as a base cloth, the base cloth is processed for water repellency, pressure-sensitive adhesive is applied as strips on one side of the base cloth in a plurality of rows separated by a prescribed gap so that the rows meander left and right over the length of the tape, the weave of the base cloth where the pressure-sensitive adhesive layer strips are formed are sealed, and permeability is maintained in the weave of the base cloth between the pressure-sensitive adhesive strips.

The base cloth comprises a warp formed by twisting a stretch thread such as a rubberized thread and a standard fiber such as cotton thread. The pressure-sensitive adhesive layers are formed in strips that meander left and right along the length of the tape. When pulled length-wise, the meanders are stretched. Since no pressure-sensitive adhesive is applied between the separate adhesive layers, stretching the warp threads of the base cloth makes the weave openings larger.

Even in a normal state, the gaps in which no pressure-sensitive adhesive is applied maintain an adequate permeability. If the gaps between the layers of pressure-sensitive adhesive were linear along the length of the tape, they would have the same length as the tape. However, the layers form meanders left and right so that the length of the gaps are considerably longer than the length of the tape. Thus, the permeability in the gaps is increased as well.

Also, since the layers of pressure-sensitive adhesive are meandered left and right rather than straight along the length of the tape, the tape can be stretched and applied while being bent in any direction without resulting in wrinkles or looseness. Since the length-wise direction of the layers of pressure-sensitive adhesive are not unidirectional, it is more uniform when tension is applied. Thus, there is good adhesive force even though the area of the pressure-sensitive adhesive layers is less than the area of the tape.

The following advantages are recognized herein for the present invention:

1. Because the base cloth is processed for water repellency, water or sweat will not adhere to or be absorbed by the tape when it is overlapping, and the upper tape of overlapping tapes will not peel off.
2. Because an acrylic-based synthetic resin is used as the base for the pressure-sensitive adhesive layers, the chemical contents of the layers will be less likely to cause skin rashes.
3. The pressure-sensitive adhesive layers are arranged in bands separated by appropriate gaps. Also, the layers meander left and right along the length of the tape. Thus, the tape can be adhered to any part of the body. Since the pressure-sensitive adhesive layers are oriented in multiple directions, it can respond to tension from multiple directions. Thus, the tape can provide good pressure-sensitive adhesion and can stretch in accordance with muscle motion.
4. The base cloth is exposed between pressure-sensitive adhesive layers so that the weave is left open. Thus, the tape has good permeability. In particular, the curves in the gaps make them significantly longer than the tape, and this provides further permeability.
5. The pressure-sensitive adhesive layers are formed with rollers. Thus, the layers can be formed easily and at low cost no matter how complex the meanderings of the layers are.

Briefly stated, the present invention provides a body-adhesive tape having adhesive properties preventing the tape from peeling off due to sweat when it is applied in an overlapped manner, and which also has good moisture permeability. In a body-adhesive tape, a base cloth is formed from a stretchable warp thread and a standard weft thread. On one side of the base cloth a plurality of pressure-sensitive adhesive layers are formed separated by appropriate gaps. The pressure-sensitive adhesive layers are formed so that they meander left and right along the length of the tape. At the gaps, the base cloth is exposed so there is permeability. Since the gap meanders, it is longer than the tape, and thus there is more exposure of the weave and more permeability. The pressure-sensitive adhesive layers meander so that the tape can be attached anywhere on the body and can respond to tension due to body movement from any direction. Base cloth is processed for water repellency so that the tapes can be attached in an overlapping manner and no sweat or the like will be absorbed, and the upper tape will not tend to peel off.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT(S)

Referring to FIGS. 1–5, the present invention has:
a body-adhesive tape, 1;
a base cloth, 2;
a warp thread, 3;
a stretch thread, 3A;
a standard fiber, 3B;
a weft thread, 4;
a pressure-sensitive adhesive layer, 5;
a gap, 6; and
a release paper, 7.

Figure 1:
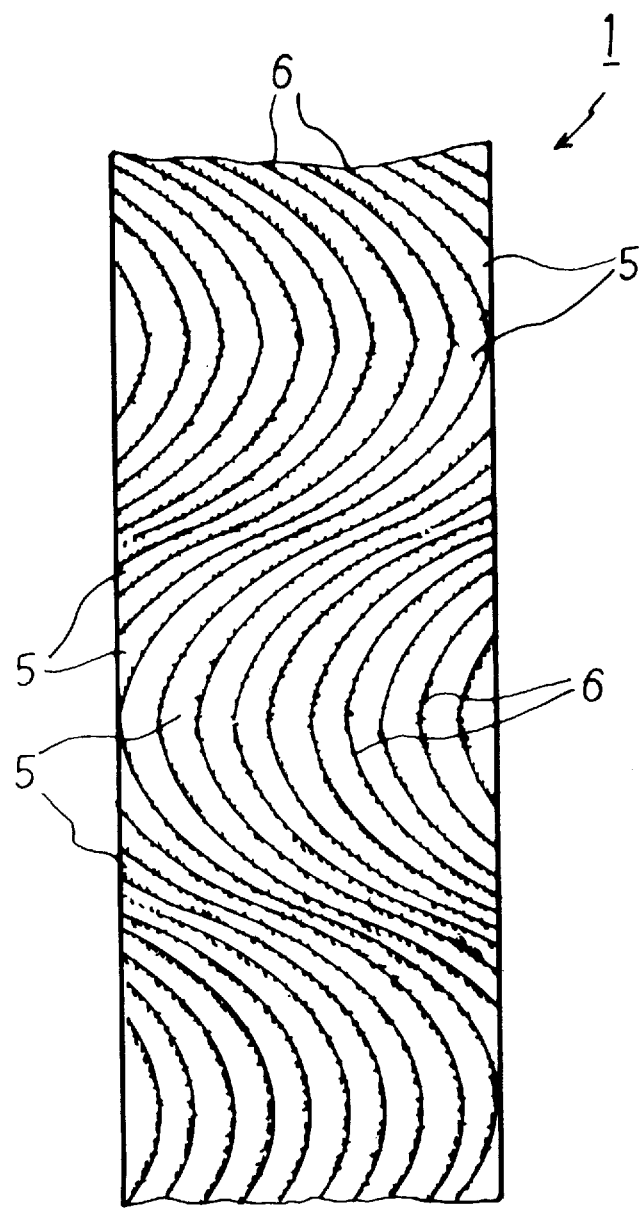
FIG. 1 is a plan drawing of the pressure-sensitive adhesive layers of the tape.
Figure 2:
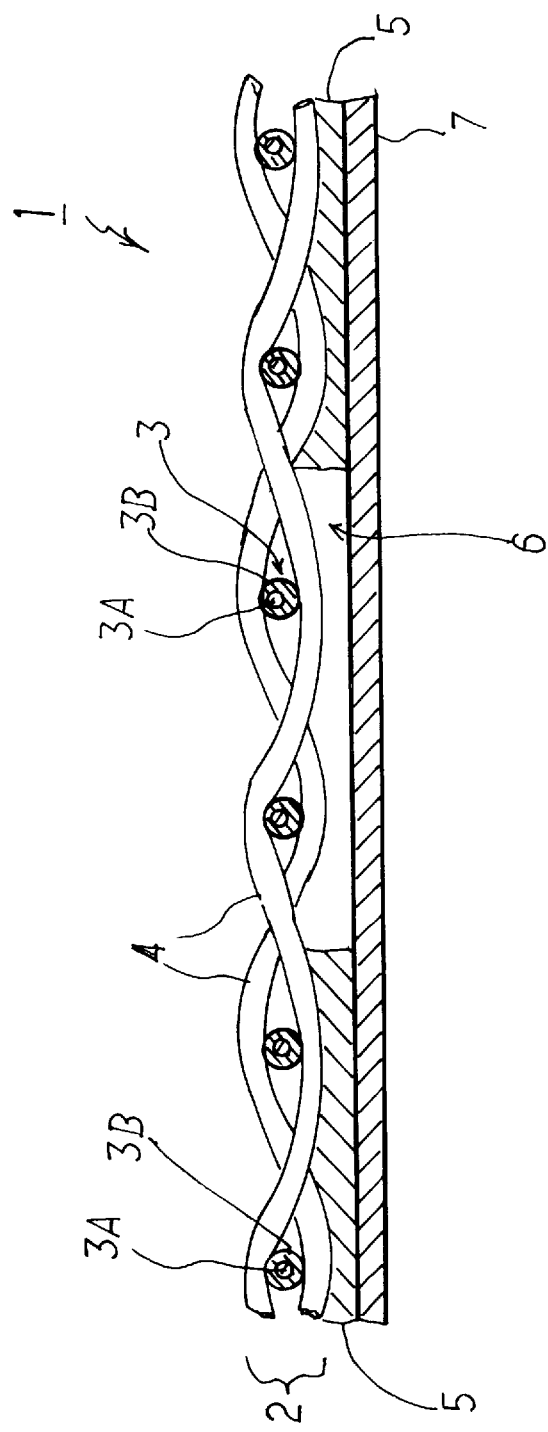
FIG. 2 is a vertical cross-section drawing of the tape.

Referring to FIG. 1, there is shown a plan drawing of a pressure-sensitive adhesive layer. Referring to FIG. 2, there is shown a cross-section drawing. In a body-adhesive tape (hereinafter referred to as tape) 1, a plurality of pressure-sensitive adhesive layers 5 comprising acrylic-based synthetic resin or the like is formed on one side of base cloth 2. Gap 6 is formed between each strip of pressure-sensitive adhesive layer 5.

Conventionally, there have been occasional cases where the plasticizer in the adhesive used in pressure-sensitive adhesive layer 5 caused skin rashes. In the present invention, an acrylic-based synthetic resin that does not tend to cause skin rashes or other irritations was used. Pressure-sensitive adhesive layers 5 are applied with a roller, so they can be formed in complicated shapes.

Warp thread 3 of base cloth 2 is made by twisting together stretch thread 3A, for example a rubberized thread, and standard fiber 3B such as a cotton thread. When warp thread 3 is pulled length-wise it can be stretched by a factor of approximately 1.7. Alternatively warp thread can be formulated of other stretchable threads including crimped fiber type stretch thread, such as a wool thread, or threads of synthetic materials that are inherently stretchable. Weft thread 4 is standard thread such as cotton thread.

Warp thread 3 is formed by twisting together stretchable thread 3A and normal thread 3B. If, for example, warp thread 3 is 100 mm long, stretch thread 3A and standard fiber 3B could be almost 170 mm in length because of the twisting and the stretch factor. The presence of standard fiber 3B ensures that when warp thread 3 is stretched, the contractive force is very small. Coventional stretchable threads are of the same length as the warp thread and so a linear contractive force is generated by the stretchable thread. In the present invention, however, stretchable thread 3A is 1.7 times as long as warp thread 3 and is twisted together with standard fiber 3B. This provides gentle stretching and compression similar to a coil spring.

Base cloth 2 is formed by using warp thread 3 and weft thread 4 to make a coarse plain weave, similar to gauze. When base cloth 2 is formed long and thin with a width of approximately 5 cm, stretching length-wise will cause base cloth 2 to stretch to the extent that warp thread 3A can stretch. When base cloth 2 is released, it will return to its original state.

Base cloth 2 is processed for water repellency using a silicon oil or the like. This makes base cloth 2 water repellent and prevents absorption of water by warp thread 3 and weft thread 4.

A plurality of pressure-sensitive adhesive layers 5 are arranged length-wise on one side of base cloth 2. Adhesive layers 5 meander to the left and right and are separated by fixed gap 6.

Adhesive layers 5 can be, for example, applied to base cloth 2 by transfer rollers. At least one of the transfer rollers would have a surface pattern of ridges and grooves identical to that of the desired pattern of adhesive layers on the base cloth 2. Adhesive would be transferred from the patterned transfer roller to base cloth 2 thereby forming the desired pattern for adhesive layers 5.

Figure 3:
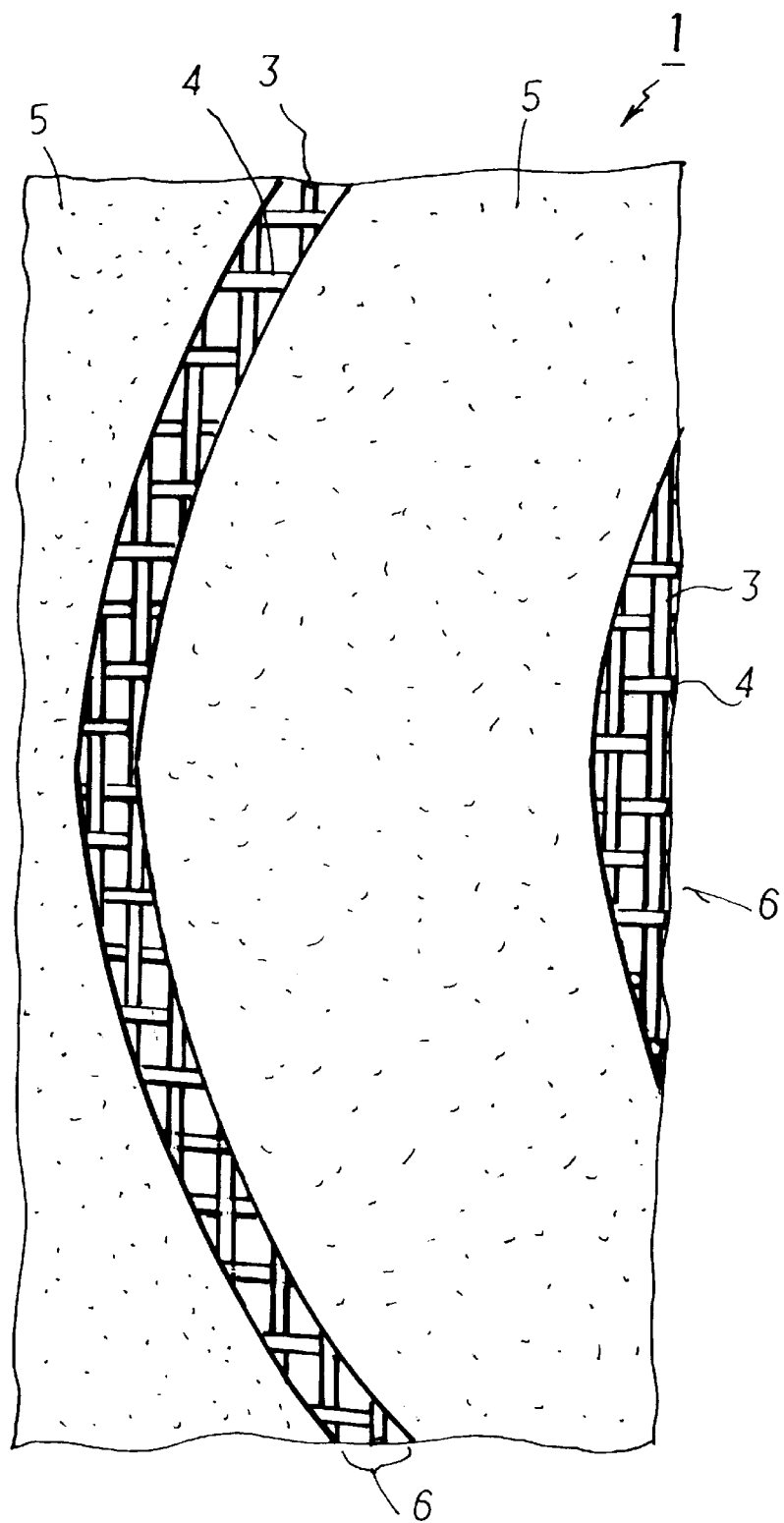
FIG. 3 is an enlarged plan drawing showing the gaps between layers of the tape.

Referring to FIG. 3, showing an enlarged plan drawing of an area around a gap 6, the weave is sealed at the areas on which pressure-sensitive adhesive layers 5 are formed, but the weave at gaps 6 is left open to maintain permeability. Referring again to FIG. 2, release paper 7 protects pressure-sensitive adhesive layer 5 while it is in storage. Release paper is removed prior to use.

Tape 1 as described above can be cut wide, e.g. about 5 cm, and at a length of about 4 meters. This can then be wrapped around a core and sold so that when tape 1 is to be used, it can be cut to an appropriate length and width.

Figure 4:
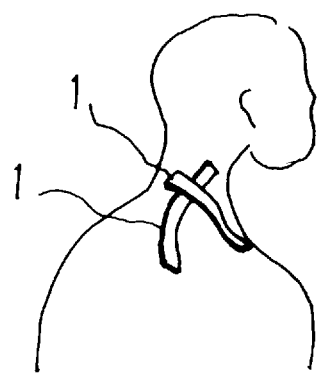
FIG. 4 is a perspective drawing showing the usage of the present invention on the neck.
Figure 5:
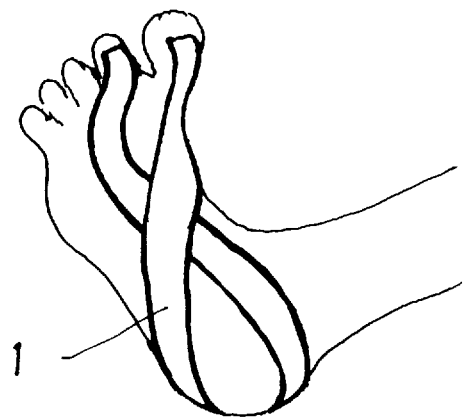
FIG. 5 is a perspective drawing showing the usage of the present invention on the foot.

Referring to FIG. 4, there is shown an example of the present invention used on the neck. Tape 1 is applied by peeling off release paper 7 and attaching it to the body. Referring to FIG. 5, there is shown an example of the present invention applied to the ankle and the sole of the foot.

Referring to FIG. 4, when a plurality of tape 1 is applied in an overlapping manner, the sweat from playing sports would be absorbed by base cloth 2 so that tape 1 at the top would peel off. However, in the present invention, base cloth 2 is processed for water repellency with silicon oil or the like. Thus, even with exposure to sweat or water, base cloth 2 will not absorb sweat or water, and pressure-sensitive adhesion can be maintained even without increasing the adhesiveness of the pressure-sensitive adhesive agent.

Referring to FIG. 1 in the context of FIG. 3, the weave of base cloth 2 is permeable at gaps 6 between adjacent pressure-sensitive adhesive layers 5 since base cloth 2 is exposed at these points. If gaps 6 were linear along the length of tape 1, the lengths of base cloth 2 and gaps 6 would be equal, but since gaps 6 meander left and right, the length of gaps 6 is longer than the length of base cloth 2. Thus, even with the same number of gaps 6, the area of base cloth 2 that is exposed is significantly more than it would be if gaps 6 were linear. Thus, permeability is improved. Also, the meandering of pressure-sensitive adhesive layers 5 allows tape 1 to be bent while attached to the body without causing problems for pressure-sensitive adhesive layers 5. Thus, tape 1 can be bent at an angle or can be bent smoothly without resulting in wrinkles or looseness.

Since tape 1 serves to protect the body, it can be applied beforehand, without stretching, to the areas most likely to be injured in sports. When muscles and skin are stretched during sports, tape 1 can stretch without effort. Since tape 1 also tends to contract, it acts to try to bring the stretching skin and corresponding muscles to its original state. This can prevent injuries arising from excessive force from the skin and muscles. Tape 1 can also prevent abrasions, cuts, and bruises.

The stretching property of base cloth 2 can be made strong, moderate, or weak by changing the stretching property of stretch thread 3A. Different types can be applied to different parts of the body. In such cases, the tapes can be distinguished by colors, such as red, yellow, and blue, so that the strength of the tape can be recognized by sight.

The widths of tape 1 can also be adjusted according to the part of the body to which it is applied. For example, widths of 2.5 cm, 4 cm, 5 cm, 7.5 cm and the like can be used. The widths and shape of pressure-sensitive adhesive layers 5 and the widths and shapes of gaps 6 can also be changed as appropriate.

Deodorants and perfumes can also be added to base cloth 2. The usage of the present invention is not restricted to sports, and can also include being used as a tool for Chinese remedies for the body, such as Kinesio taping for chiropractic remedies.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A body-adhesive tape comprising:

a water-repellent base cloth formed from a warp thread and a weft thread;

said warp thread including a stretch thread twisted together with a standard fiber;

said weft thread being a non-elastic thread;

a plurality of wavy strip-shaped pressure-sensitive adhesive layers formed on one side of said base cloth;

said adhesive layers arranged in rows separated by prescribed gaps;

said base cloth being exposed in said gaps;

said adhesive layers varying in width at a plurality of locations along said length in a direction transverse to said length of said tape;

said adhesive layers and said gaps covering substantially the whole surface of said tape;

said base cloth having lower permeability at portions on which said pressure-sensitive adhesive layers are formed; and said base cloth having higher permeability at said prescribed gaps separating said adhesive layers.

2. A body-adhesive tape as described in claim 1, wherein said pressure-sensitive adhesive layer includes an acrylic-based synthetic resin.

* * * * *